(12) United States Patent
Fan et al.

(10) Patent No.: US 9,358,001 B2
(45) Date of Patent: *Jun. 7, 2016

(54) ADVANCE SUTURE PASSER

(71) Applicant: SMITH & NEPHEW, INC., Memphis, TN (US)

(72) Inventors: Wei Li Fan, Malden, MA (US); Linh Nguyen, Randolph, MA (US); Jim Sullivan, Shrewsbury, MA (US)

(73) Assignee: Smith & Nephew, Inc., Memphis, TN (US)

( * ) Notice: Subject to any disclaimer, the term of this patent is extended or adjusted under 35 U.S.C. 154(b) by 220 days.

This patent is subject to a terminal disclaimer.

(21) Appl. No.: 14/087,920

(22) Filed: Nov. 22, 2013

(65) Prior Publication Data

US 2014/0088617 A1 Mar. 27, 2014

Related U.S. Application Data

(63) Continuation of application No. 13/093,248, filed on Apr. 25, 2011, now Pat. No. 8,591,527.

(51) Int. Cl.
*A61B 17/04* (2006.01)
*A61B 17/06* (2006.01)
*A61B 17/00* (2006.01)

(52) U.S. Cl.
CPC . *A61B 17/06109* (2013.01); *A61B 2017/00867* (2013.01); *A61B 2017/0495* (2013.01); *A61B 2017/06009* (2013.01); *A61B 2017/06019* (2013.01); *A61B 2017/06042* (2013.01)

(58) Field of Classification Search
CPC ............... A61B 17/06109; A61B 2017/06009; A61B 2017/06042; A61B 2017/06019
See application file for complete search history.

(56) References Cited

U.S. PATENT DOCUMENTS

| 4,441,497 A | 4/1984 | Paudler |
| 4,781,190 A | 11/1988 | Lee |
| 5,454,823 A | 10/1995 | Richardson et al. |

(Continued)

FOREIGN PATENT DOCUMENTS

| EP | 2353516 A1 | 8/2011 |
| WO | 2009138103 A1 | 11/2009 |

OTHER PUBLICATIONS

International Search Report dated Jul. 9, 2012, PCT/US2012/034706, 2 pages.

(Continued)

*Primary Examiner* — Julian W Woo
(74) *Attorney, Agent, or Firm* — Burns & Levinson LLP; Joseph M. Maraia

(57) ABSTRACT

A suture passer including a tubular member having a proximal end and a distal end and a central axis defined therethrough, in which the tubular member includes at least one lumen formed therein, an eyelet configured to receive a suture, a movable jaw formed on the distal end of the tubular member configured to move between an open position and a closed position, in which the movable jaw includes a plurality of portions, and an actuator configured to be received within the at least one lumen of the tubular member, in which the actuator is configured to move along the central axis of the tubular member between a first position and a second position, in which, in the first position, the movable jaw is in the closed position, and in which, in the second position, the movable jaw is in the open position.

15 Claims, 17 Drawing Sheets

(56) References Cited

U.S. PATENT DOCUMENTS

| | | |
|---|---|---|
| 5,573,008 A | 11/1996 | Robinson |
| 5,730,747 A | 3/1998 | Ek et al. |
| 5,899,911 A | 5/1999 | Carter |
| 5,935,149 A | 8/1999 | Ek |
| 6,051,006 A | 4/2000 | Shluzas et al. |
| 6,383,199 B2 * | 5/2002 | Carter ............... A61B 17/0057 606/148 |
| 7,585,305 B2 | 9/2009 | Dreyfuss |
| 8,591,527 B2 * | 11/2013 | Fan ............... A61B 17/06109 606/144 |
| 2002/0055758 A1 | 5/2002 | Sasaki |
| 2002/0173800 A1 | 11/2002 | Dreyfuss et al. |
| 2002/0193811 A1 | 12/2002 | Chan |
| 2004/0249393 A1 | 12/2004 | Weisel et al. |
| 2004/0260314 A1 | 12/2004 | Lizardi et al. |
| 2007/0118152 A1 | 5/2007 | Page |
| 2008/0027468 A1 | 1/2008 | Fenton et al. |
| 2009/0018554 A1 | 1/2009 | Thorne et al. |
| 2009/0062819 A1 | 3/2009 | Burkhart et al. |
| 2009/0069824 A1 | 3/2009 | Chu |
| 2009/0082788 A1 | 3/2009 | Elmaraghy |
| 2009/0131956 A1 | 5/2009 | Dewey et al. |
| 2010/0042117 A1 | 2/2010 | Kim et al. |

OTHER PUBLICATIONS

Communication for related European Application No. 12717031.4 mailed Nov. 23, 2015.

* cited by examiner

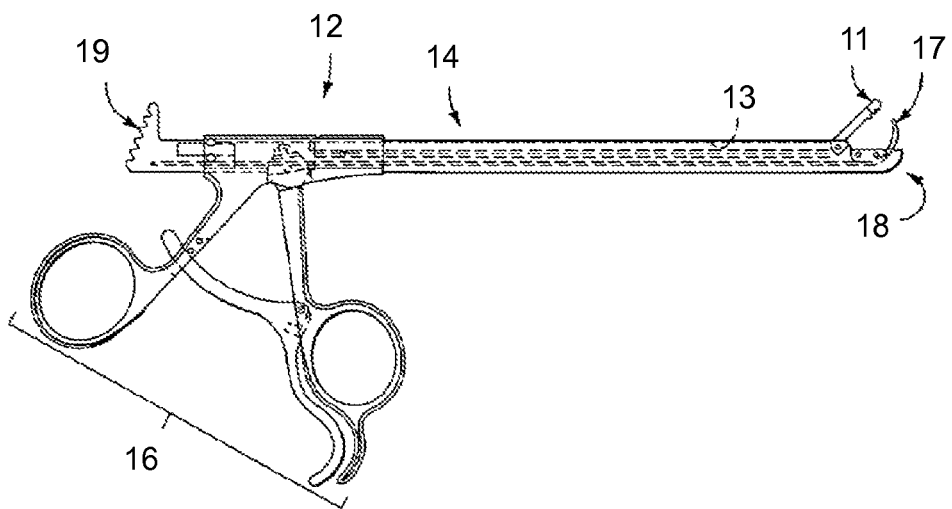
FIG.. 1A
Prior Art

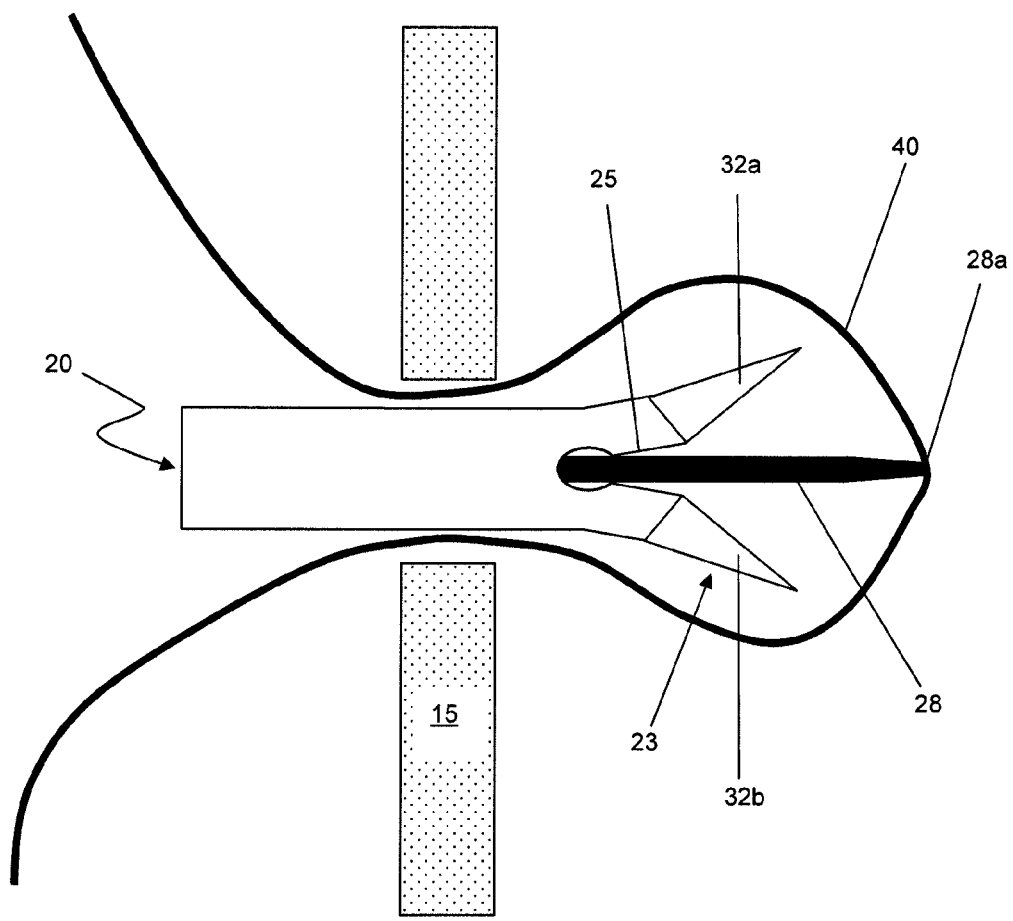

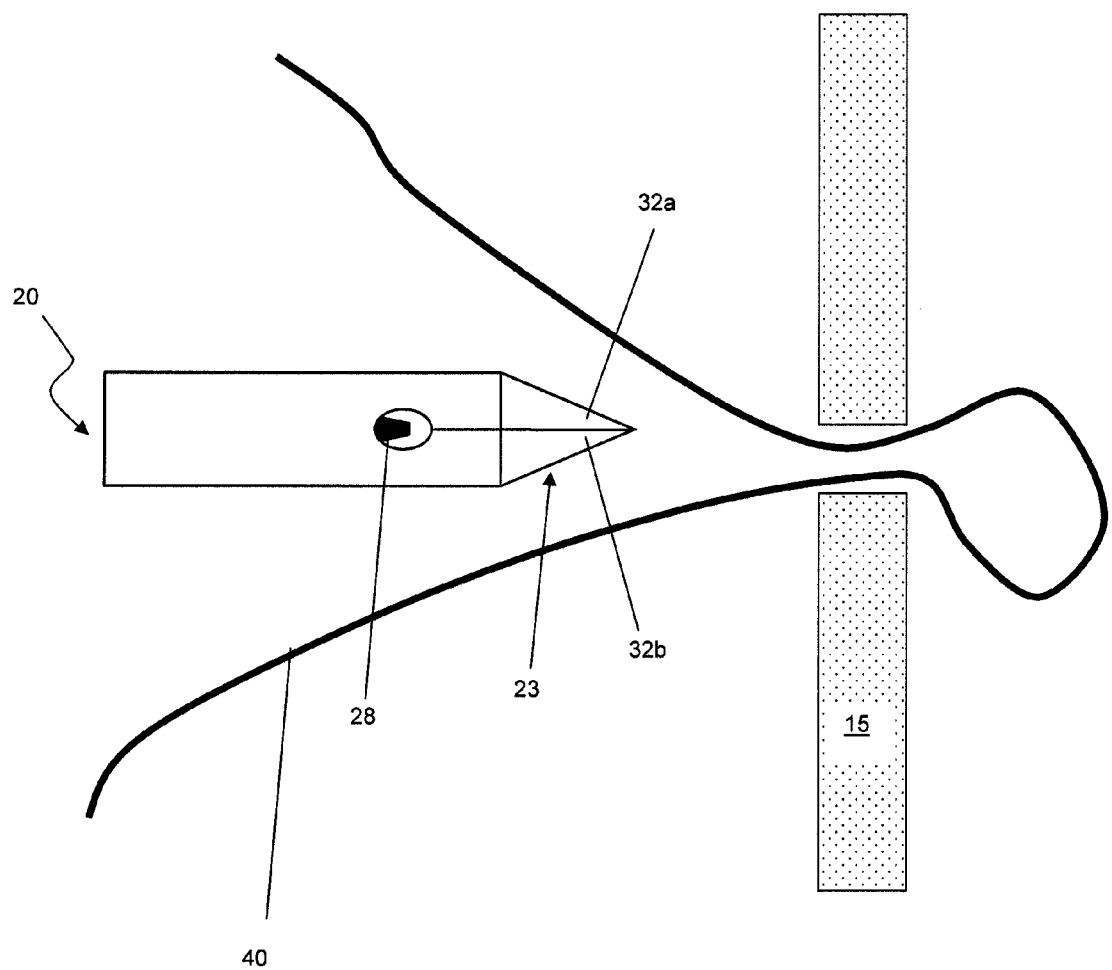

ADVANCE SUTURE PASSER

RELATED APPLICATIONS

This patent application is a continuation of U.S. patent application Ser. No. 13/093248, filed Apr. 25, 2011, now U.S. Pat. No. 8,591,527, the entire contents of which is incorporated herein by reference.

BACKGROUND OF INVENTION

1. Field of the Invention

The invention relates generally to suture passing surgical instruments and methods of passing sutures through tissues.

2. Background Art

Both open and endoscopic surgical procedures often require sutures to ligate, join or otherwise treat tissue. Sutures can be passed through tissues in many ways including cannulated needles and instruments and needle passing instruments, which usually require the use of multiple portal entry points to transfer sutures through tissues or require the use of additional instruments or devices to facilitate the passage of sutures.

In general, suture needles with attached sutures may be grasped either manually or by forceps and passed through the desired work site so knots can be tied. While the procedures are fairly simple in open surgery where most suture sites are readily accessible, in endoscopic procedures, where access to the work site may not be readily available, the surgeon may need to use auxiliary devices to grasp sutures and pass them through desired tissue.

Various instruments and techniques have been developed for surgical repairs requiring passing sutures to distant locations. For example, U.S. Pat. No. 4,781,190 to Lee discloses a two-ended needle enabling arthroscopic suturing of the interior of a joint. The two-ended needle may be either straight or curved and may be provided with eyelet intermediates at the ends of the needle. Sutures can be passed through eyelets of the needle and then through tissues by alternately passing the ends of the needle through tissues to be sutured.

U.S. Pat. No. 4,441,497 to Paudler discloses a suture passer having a plurality of flexible elongated members joined at their corresponding ends, the ends being sharpened enough to pass through desired tissue sites. Pushing the ends toward each other opens up spaces between the members into which one or more sutures may be placed. Moving the ends of the flexible members away from each other closes up the spaces to grip the sutures so that the ends of the flexible members and, consequently, the sutures, may be passed through the desired suture sites.

Referring to FIGS. 1A-1B, yet another example of a suture-advancing device as disclosed by U.S. Pat. No. 7,585,305 to Dreyfuss is shown. FIG. 1A shows the suture-advancing device 12, which includes body 14 housing shape-memory wire 17, jaw 11, hand mechanism 16 for articulating jaw 11 relative to tip 18, actuator 13, and pusher 19 for advancing wire 17 through body 14 and tip 18. FIG. 1B shows that, by actuating the hand mechanism, a surgeon may seize and maintain tissue 15 with jaw 11 and the tip and, using the pusher to urge wire 17 to push suture 10 through tissue 15.

There remains a need for improved suture passers that allow sutures to pass through tissues with minimal damage to the tissues.

SUMMARY OF INVENTION

According to one aspect of the present invention, there is provided a suture passer including a tubular member having a proximal end and a distal end and a central axis defined therethrough, in which the tubular member includes at least one lumen formed therein, an eyelet configured to receive a suture, a movable jaw formed on the distal end of the tubular member configured to move between an open position and a closed position, in which the movable jaw includes a plurality of portions, in which the plurality of portions are biased to the closed position, and an actuator configured to be received within the at least one lumen of the tubular member, in which the actuator is configured to move along the central axis of the tubular member between a first position and a second position, in which, in the first position, the movable jaw is in the closed position, and in which, in the second position, the movable jaw is in the open position.

According to another aspect of the present invention, there is provided a method of suturing including providing a suture passer, passing a first suture through an eyelet of the suture passer, piercing a first region of a tissue with the suture passer, moving an actuator of the suture passer into a second position, in which the actuator engages the first suture when the actuator moves between the first position and the second position, in which, in the second position, the movable jaw is in the open position, and disposing the first suture, at least partially, within the tissue. The suture passer may include a tubular member having a proximal end and a distal end and a central axis defined therethrough, in which the tubular member includes at least one lumen formed therein, an eyelet configured to receive at least one suture, a movable jaw formed on the distal end of the tubular member configured to move between an open position and a closed position, an actuator configured to be received within the at least one lumen of the tubular member, in which the actuator is configured to move along the central axis of the tubular member between a first position and a second position, and in which the actuator is initially in the first position.

Other aspects and advantages of the invention will be apparent from the following description and the appended claims.

BRIEF DESCRIPTION OF DRAWINGS

FIG. 1A shows a side view of a conventional suture passing instrument.

FIG. 4B shows an environment perspective view of a suture passer with a suture in accordance with embodiments of the invention after piercing through a tissue.

FIG. 4C shows an environment perspective view of a retracting suture passer in accordance with embodiments of the invention after releasing a suture.

DETAILED DESCRIPTION

Embodiments in accordance with the invention relate to devices and methods for passing sutures. Embodiments of the invention may be used in any surgical procedures that require passing sutures. For clarity of illustration, the following description will use suture passers and retrievers in accordance with embodiments disclosed herein to pass sutures, such as, but not limited to, braided sutures, through easy-to-reach tissues, such as piercing through labrum. However, one having ordinary skill in the art will appreciate that the same approaches may be applied to difficult-to-reach tissues, in which embodiments disclosed herein may be modified without departing from the spirit or scope of the present invention.

Figure 1B:
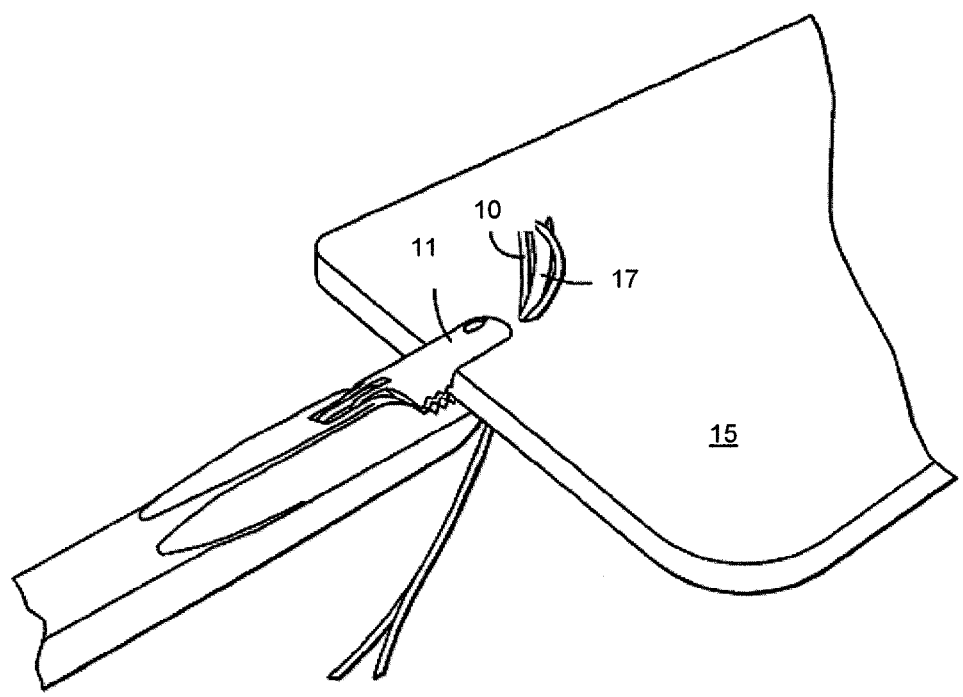
FIG. 1B shows an environment perspective view of the suture passing instrument shown in FIG. 1A with the wire having urged suture through tissue.
Figure 2A:
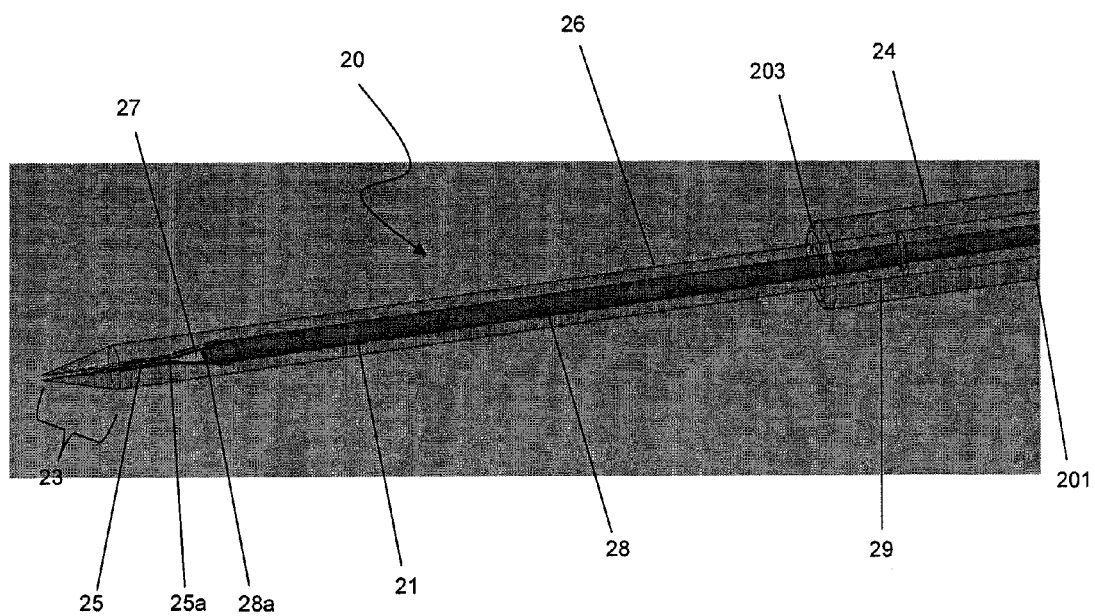
FIG. 2A shows a suture passer in accordance with embodiments of the invention.

Referring to FIG. 2A, a suture passer 20 in accordance with embodiments disclosed herein is shown. In one or more embodiments, the suture passer 20 may include a tubular shaft 24, a tubular member 26 having a proximal end and a distal end and a central axis defined therethrough, and an actuator 28. As shown, the tubular member 26 may include at least one lumen 21 formed therein, an eyelet 27 configured to receive a suture, a movable jaw 23 formed on the distal end of the tubular member, and a slot 25 formed between the eyelet and the movable jaw. In one or more embodiments, the movable jaw 23 may be configured to move between an open position and a closed position. In one or more embodiments, the actuator 28 may be configured to be received within the at least one lumen 21 of the tubular member 26. In one or more embodiments, the actuator 28 may be configured to move along the central axis of the tubular member between a first position and a second position. In one or more embodiments, the actuator 28 may be slidingly movable within tubular shaft 24 and the lumen 21 of the tubular member 26 in a direction that is parallel with the central axis of the tubular member 26. Although the tubular member 26 is shown having at least one lumen 21, those having ordinary skill in the art will appreciate that the tubular member 26 of the suture passer 20 may include more or less lumens formed therein than described above. For example, the tubular member 26 may have two, three, four, or more lumens formed therein. Further, in one or more embodiments, the tubular member 26 may be made of a flexible material having a shape memory property. For example, in one or more embodiments, the tubular member 26 of the suture passer 20 may be composed of one of nitinol, a polymer, a plastic, and a flexible stainless steel. Further, in one or more embodiments, the tubular member 26 may include an external surface, in which the external surface may include one of a smooth surface, a serrated surface, and a ridged surface.

In one or more embodiments, the tubular shaft 24 may be a tubular shaft of any shape having a longitudinally axial throughbore 29 formed therein, configured to receive the tubular member 26 and the actuator 28. In one or more embodiments, the tubular shaft 24 may have a proximal end 201 and a distal end 203, in which the distal end of the tubular shaft may be coupled to a proximal end of the tubular member 26. The tubular shaft 24 may be made of any suitable materials, such as stainless steel, plastics, and polymers.

In one or more embodiments, the actuator 28 may have a distal end 28a, which may be received by a proximal end 25a of the slot 25 (with or without a suture) and may separate the slot 25 to move the movable jaw 23 into the open position. Conversely, the actuator 28 may be retracted to move the movable jaw 23 into the closed position. As discussed above, the actuator 28 may be configured to be received within the at least one lumen 21 of the tubular member 26 and may be configured to move along the central axis of the tubular member between a first position and a second position. In one or more embodiments, when the actuator 28 is in the first position, the actuator 28 may not be engaged with the movable jaw 23. Accordingly, when the actuator 28 is in the first position, the movable jaw 23 may be in the closed position. In the first position, the actuator 28 may or may not contact, or be engaged with, a suture (not shown). Further, in one or more embodiments, when the actuator 28 is in the second position, the actuator 28 may be engaged with the movable jaw 23 and may move portions of the movable jaw 23 to move or separate, discussed further below. Accordingly, when the actuator 28 is in the second position, the movable jaw 23 may be in the open position. In the second position, the actuator 28 may be engaged with a suture. The distal end 28a of the actuator 28 may have a width (or diameter, if actuator 28 is a rod) of at least the diameter of one suture. Those having ordinary skill in the art will appreciate that the suture size, as well as the diameter or width of the actuator may be any size known in the art. For example, the suture size may be 0.020-0.029 mm in diameter. In one or more embodiments, the suture size may be 0.022-0.024 mm in diameter.

In one or more embodiments, the actuator 28 may be advanced, or moved along the central axis of the tubular member 26 or moved in a direction that is parallel to the central axis of the tubular member 26, to contact at least one suture (not shown) disposed through the eyelet 27. In one or more embodiments, the actuator 28 may be in the first position, and may advance the distal end 28a of the actuator 28 to contact the at least one suture disposed therethrough the eyelet 27. When actuator 28 advances from the first position to the second position, which is different from the first position, the distal end 28a of the actuator 28 may contact the proximal end 25a of the slot 25 and may cause, urge, force, or move the movable jaw 23 to move into the open position and push the at least one suture through the slot 25 and through the movable jaw 23. Those having ordinary skill in the art will appreciate that an actuator, according to embodiments disclosed herein, may be any member, device, or mechanism that may cause, urge, force, or move the movable jaw 23 between the open position and the closed position and may contact or engage with a suture and move or advance the suture through a proximal end of the tubular member 26, e.g., through a proximal end of the movable jaw 23.

Figure 2B:
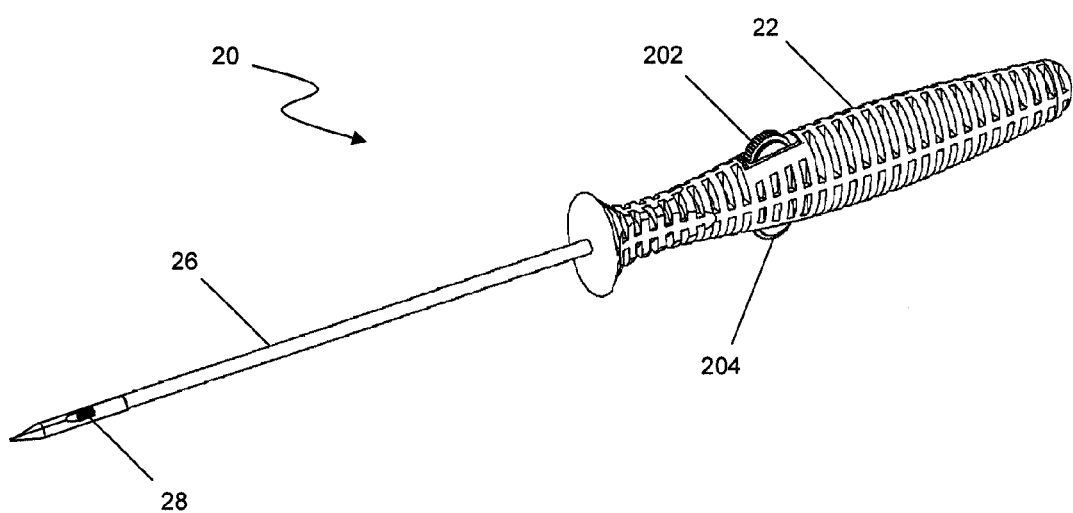
FIG. 2B shows a perspective view of a suture passer in accordance with embodiments of the invention.

Referring to FIG. 2B, a suture passer in accordance with embodiments disclosed herein is shown. In one or more embodiments, the tubular member 26 of the suture passer 20 may be coupled to a handle 22. Specifically, in one or more embodiments, a proximal end of the tubular member 26 may be coupled to the handle 22. In one or more embodiments, the actuator 28 may be coupled to the handle 22, and the handle 22 may be substantially in-line with the central axis of the tubular member 26 and may include one or more control mechanisms. For example, as shown, the handle 22 may include wheels 202 and 204. In one or more embodiments, the wheels 202 and 204 may cooperate to advance or retract the actuator 28 along the central axis of the tubular member 26. Those having ordinary skill in the art will appreciate that other suitable manual or mechanized mechanisms may also be adapted to advance or retract the actuator 28 along the central axis of the tubular member 26 or move the actuator in a direction that is parallel to the central axis of the tubular member 26. For example, the handle 22 of the suture passer 20 may include one or more push buttons and/or one or more slidable buttons that may move, advance, or retract the actuator 28 in a direction that is parallel to the central axis of the tubular member 26. Other handles in accordance with one or more embodiments disclosed herein include pistol-grip handles, which may be substantially perpendicular to the central axis of the tubular member 26. Examples of pistol-grip handles include those disclosed in U.S. Pat. Nos. 5,730,747, 5,935,149, and 6,051,006, which are herein incorporated by reference in their entirety.

Figure 3A:
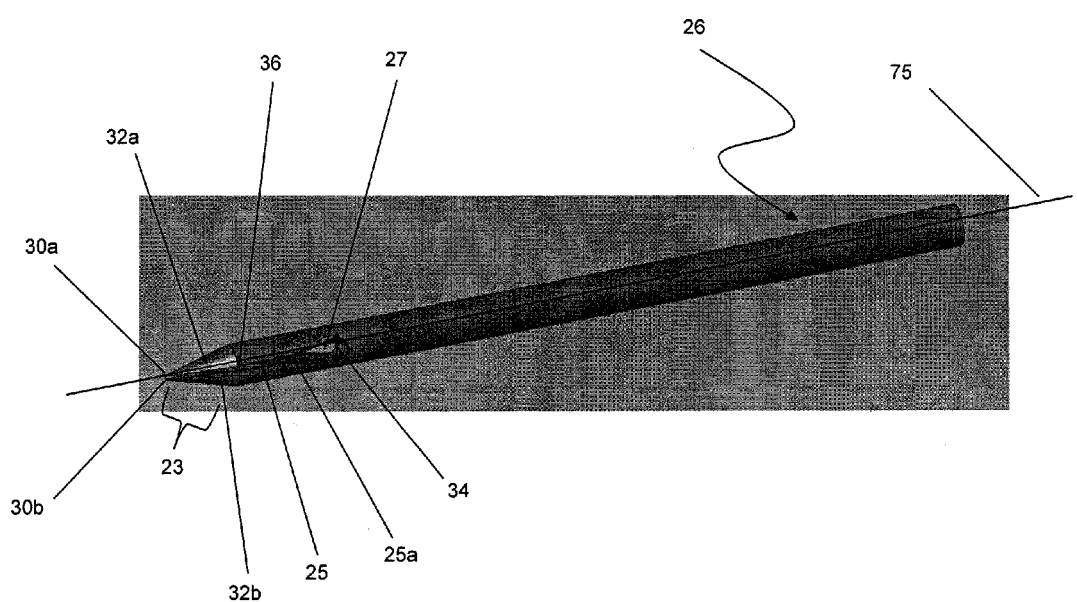
FIG. 3A shows geometry of a tubular member in accordance with embodiments of the invention.

Referring to FIG. 3A, geometry of the tubular member 26 in accordance with embodiments disclosed herein is shown. As shown, the eyelet 27 may have a width 34 of at least the diameter of one suture (not shown), allowing at least one suture to pass therethrough, or be disposed therein, and pass through the tubular member 26. In one or more embodiments, the eyelet 27 may communicate with the movable jaw 23 through the slot 25, which may form a passage allowing a suture to be advanced through the tubular member 26 by an actuator (not shown) from the eyelet 27 to a proximal end 36 of the movable jaw 23, e.g. in a direction that is parallel with a central axis 75 of the tubular member 26. In one or more embodiments, the diameter of the lumen (not shown) of the tubular member 26 may gradually decrease from the eyelet 27 to a minimum diameter, e.g. the width or diameter of the slot 25, at a proximal end 25a of the slot 25 or at a distal end of the movable jaw 23.

As discussed above, the tubular member 26 may be made of any suitable flexible materials that have shape memory properties and super-elasticity, such as nitinol, polymers, and flexible stainless steel. Further, in one or more embodiments, an external surface of the tubular member 26 and/or the movable jaw 23 may include any patterns and shapes, such as a smooth surface, a serrated surface, and a ridged surface, or any combination thereof, suitable for piercing through tissues.

Still referring to FIG. 3A, in one or more embodiments, the movable jaw 23 may be formed by a plurality of portions that may be configured to converged to at least one end, such as bifurcated portions 32a, 32b with two ends 30a, 30b. In one or more embodiments, the movable jaw 23 is in an open position when bifurcated portions 32a, 32b are in a separated relationship. In one or more embodiments, the plurality of portions, e.g., the bifurcated portions 32a and 32b of the movable jaw 32, may form a non-conical shape when the movable jaw 23 is in the open position. Further, in one or more embodiments, the movable jaw 23 is in a closed position when bifurcated portions 32a, 32b are in a proximate relationship. In one or more embodiments, the movable jaw 23 may be biased to a closed position. For example, the plurality of portions, e.g., the bifurcated portions 32a and 32b may be biased to the closed position, in which the bifurcated portions 32a and 32b are in a proximate relationship. In one or more embodiments, when the bifurcated portions 32a and 32b are in a proximate relationship, the bifurcated portions 32a and 32b may be separated by a distance that forms the slot 25. In other words, the width, or diameter, of the slot 25 may be a distance separating the portions of the movable jaw 23, e.g., the bifurcated portions 32a and 32b. Alternatively, in one or more embodiments, when the bifurcated portions 32a and 32b are in a proximate relationship, the bifurcated portion 32a may be engaged with the bifurcated portion 32b, in which a slot may not be formed between the eyelet 27 and the two ends 30a and 30b of the bifurcated portions 32a and 32b. In one or more embodiments, when the movable jaw 23 is in a closed position, bifurcated portions 32a, 32b may form a conical shape. In one or more embodiments, when the movable jaw 23 is in the closed position, bifurcated portions 32a and 32b, e.g., the plurality of portions, may be configured to converge to at least one pointed end. Those having ordinary skill in the art will appreciate that other jaw shapes, such as non-conical shape, may be adapted for efficient penetration through tissues.

Figure 3B:
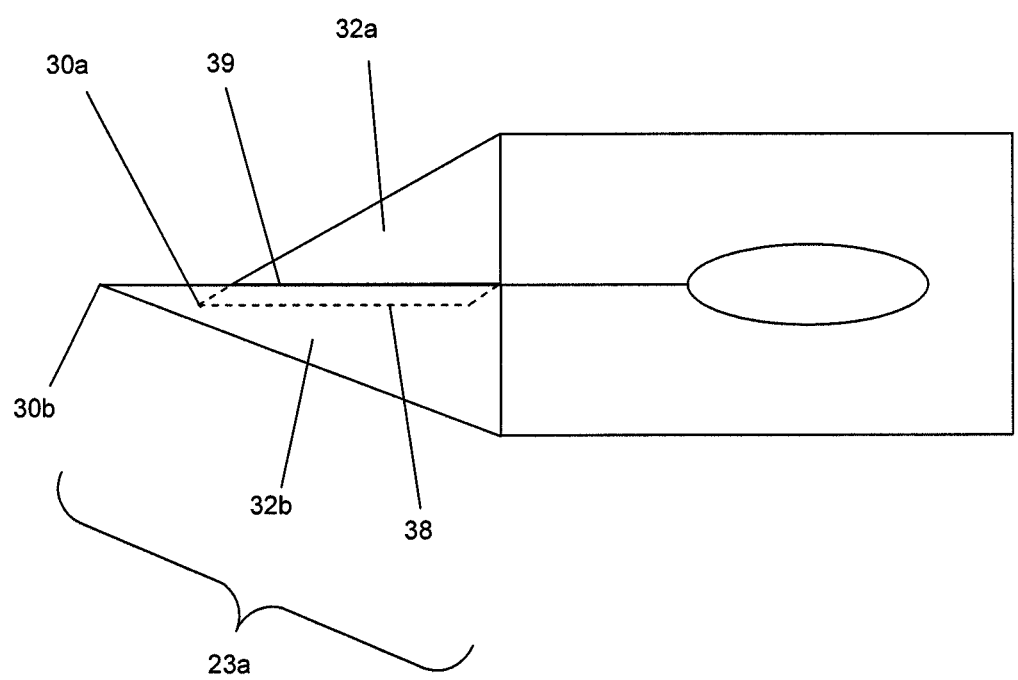
FIG. 3B shows a side view of a movable jaw of a suture passer in accordance with embodiments of the invention

Referring to FIG. 3B, a side view of a movable jaw 23a in accordance with embodiments disclosed herein is shown. As shown, the movable jaw 23a is in a closed position. In one or more embodiments, the bifurcated portions 32a, 32b may form a non-conical shape. For example, as shown, when the movable jaw 23a is in the closed position, the portion 32a may have a first length that is shorter than a second length of the portion 32b. In other words, the bifurcated portions 32a and 32b may form a non-conical shape in the closed position, in which one of the bifurcated portions, e.g., the bifurcated portion 32b, includes a first length that is larger than a second length of another of the bifurcated portions, e.g. the bifurcated portion 32a. As such, an edge 38 of the portion 32a may be even with, or may overlap, an edge 39 of the portion 32b. In one or more embodiments, the movable jaw 23a with a non-conical shape may be beneficial to prevent tissues from being trapped between ends 30a, 30b of the portions 32a and 32b during the process of passing sutures through tissues.

A method of suturing, according to embodiments disclosed herein, may include providing a suture passer, passing a first suture through an eyelet of the suture passer, piercing a first region of a tissue with the suture passer, moving an actuator of the suture passer into a second position, in which the actuator engages the first suture when the actuator moves between the first position and the second position, in which, in the second position, the movable jaw is in the open position, and disposing the first suture, at least partially, within the tissue. As discussed above, the suture passer may include a tubular member having a proximal end and a distal end and a central axis defined therethrough, in which the tubular member includes at least one lumen formed therein, an eyelet configured to receive at least one suture, a movable jaw formed on the distal end of the tubular member configured to move between an open position and a closed position, an actuator configured to be received within the at least one lumen of the tubular member, in which the actuator is configured to move along the central axis of the tubular member between a first position and a second position, and in which the actuator is initially in the first position.

The method of suturing, in accordance with embodiments disclosed herein, may also include releasing the first suture, moving the actuator into the first position, in which, in the first position, the movable jaw is in the closed position; and removing the suture passer from the tissue. In one or more embodiments, releasing the first suture may include disengaging the first suture from the actuator, in which the first suture forms a first suture loop, at least partially, within the tissue. The method may also include providing at least one graft to be bound to the tissue, engaging at least one graft with the tissue, engaging the at least suture with the at least one graft, piercing a second region of the tissue with the suture passer, moving the actuator into the second position, in which, in the second position, the movable jaw is in the open position, and disposing the first suture, at least partially, within the tissue. The method may also include releasing the first suture, moving the actuator into the first position, in which, in the first position, the movable jaw is in the closed position, and removing the suture passer from the tissue. In one or more embodiments, releasing the first suture comprises disengaging the first suture from the actuator, in which the first suture forms a second suture loop, at least partially, within the tissue. The method may also include threading a second suture through the first suture loop and the second suture loop of the first suture, and stabilizing the at least one graft with the tissue. In one or more embodiments, stabilizing the at least one graft with the tissue may include tightening the first suture and the second suture, causing the at least one graft to be bound against the tissue. Finally, in one or more embodiments, the first suture and the second suture are the same suture.

Figure 4A:
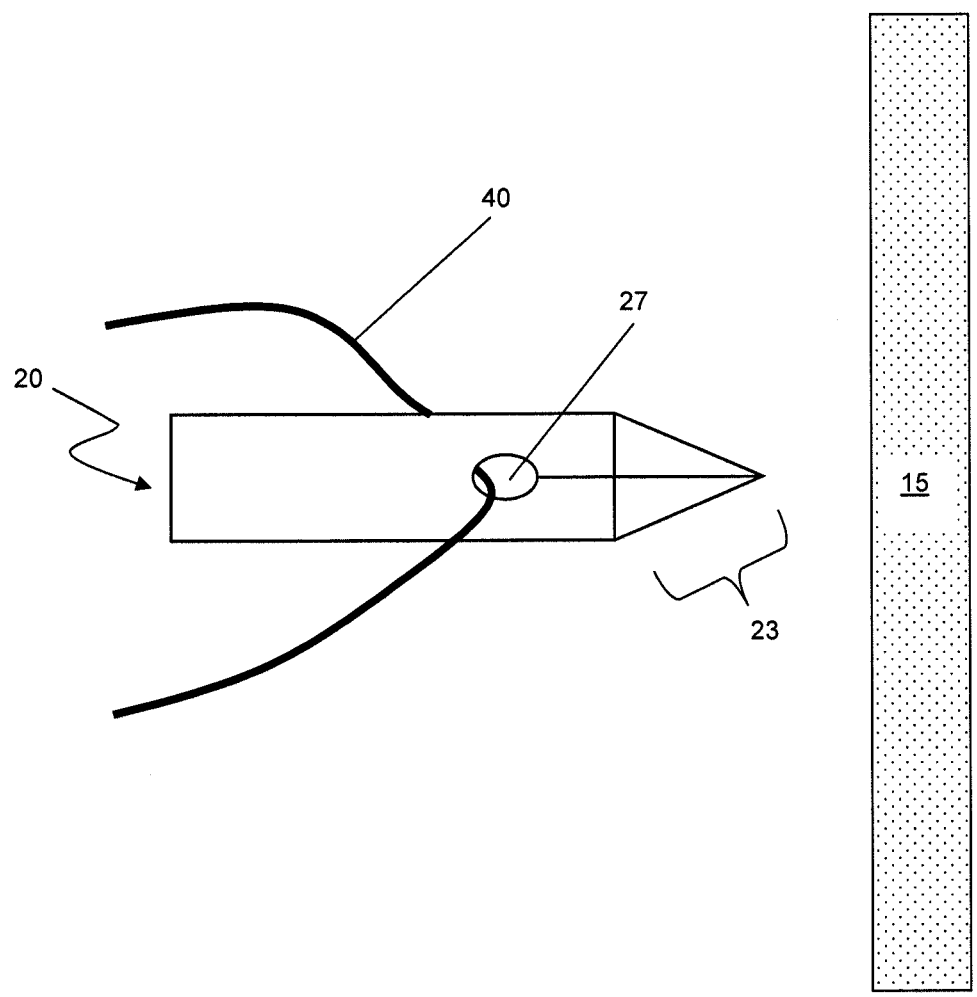
FIG. 4A shows an environment side view of a suture passer with a suture in accordance with embodiments of the invention prior to piercing through a tissue.

FIGS. 4A-4C show a method of passing suture through tissues in accordance with embodiments disclosed herein.

Referring to FIG. 4A, a suture 40 disposed through the eyelet 27 of the suture passer 20 prior to piercing through a tissue 15 is shown. As discussed above, the eyelet 27 configured to receive a suture. As shown, the movable jaw 23 of the suture passer 20 is in the closed position. Further, as discussed above, the actuator (not shown) may be in the first position, in which the actuator may or may not be engaged with the suture 40. In one or more embodiments, when the actuator is in the first position, the actuator may not be engaged with the movable jaw 23, and the movable jaw 23 may be in the closed position, as shown. Further, when the actuator is in the first position, the actuator may or may not be contacting, or engaged with, the suture 40. In other words, as shown, the actuator may not necessarily be in contact the suture 40 and may still be in the first position. Alternatively, the actuator may be in contact with, or engaged with, the suture 40 in the first position.

Referring to FIG. 4B, an environment perspective view of the suture passer 20 with the suture 40 in accordance with embodiments disclosed herein, after piercing through a tissue, is shown. As shown, the movable jaw 23 is in the open position and the actuator 28 is in the second position. As discussed above, when the actuator 28 is in the second position, the movable jaw 23 may be in the open position. Further, as discussed above, the bifurcated portions 32a and 32b may form a non-conical shape when the movable jaw 23 is in the open position. Furthermore, as discussed above, the distal end 28a of the actuator 28 may contact, or be engaged with, the suture 40 and may contact the proximal end of the slot 25 and may cause, urge, or force, the movable jaw 23 to move into the open position and push the at least one suture through the slot 25 and through the movable jaw 23, as shown. In other words, as shown, the suture passer 20 has pierced through the tissue 15, and the actuator 28, having the distal end 28a configured to have a width (or diameter) greater than the width (or a diameter of lumen) of the slot 25, to urge the bifurcated portions, 32a, 32b to be in a separated relationship, e.g. to move the movable jaw 23 into the open position and release suture 40. In one or more embodiments, releasing the suture 40 may include disengaging the suture 40 from the actuator 28, in which the suture 40 forms a suture loop, at least partially, within the tissue 15. Those having ordinary skill in the art will appreciate that a suture loop, as described herein, may not necessarily be a closed loop. For example, the suture 40, as shown in FIGS. 4B and 4C, form a suture loop within the tissue 15.

Referring to FIG. 4C, an environment perspective view of a retracting suture passer 20 in accordance with embodiments disclosed herein, after releasing a suture 40, is shown. As shown, the actuator 28 is in the first position and the movable jaw 23 is in the closed position. As discussed above, the bifurcated portions 32a and 32b may be in a proximate relationship when the movable jaw 23 is in the closed position. Further, as shown and discussed above, the actuator 28 may be in the first position and may not necessarily be contacting, or engaged with, the suture 40. In one or more embodiments, the suture passer 20 may be withdrawn from within the tissue 15 and the suture 40 may form a suture loop and may remain disposed within the tissue 15, as shown. In other words, after releasing the suture 40, the actuator 28 may be retracted within the suture passer 20, which may allow the bifurcated portions, 32a, 32b of the movable jaw 23 to return to the closed position and to be in a proximate relationship. The suture passer 20 may, subsequently, be removed from tissue 15.

Figure 5:
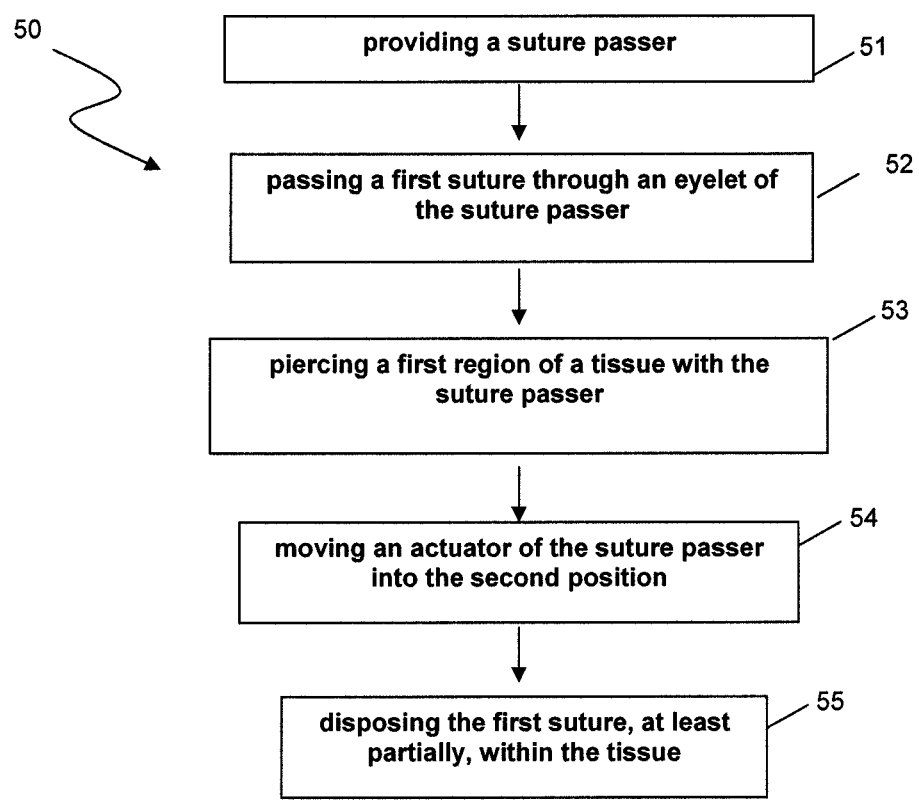
FIG. 5 shows a method of passing a suture in accordance with embodiments of the invention.

Referring to FIG. 5, a workflow 50 of passing suture through tissues in accordance with embodiments disclosed herein is shown. Workflow 50 may include providing a suture passer, in accordance with embodiments disclosed herein, 51; passing, loading, or disposing a first suture through an eyelet of the suture passer, 52; piercing a first region of a tissue with the suture passer, 53; moving an actuator of the suture passer into a second position, 54; and disposing the first suture, at least partially, within the tissue, 55. In one or more embodiments, piercing a first region of a tissue with the suture passer may include piercing the first region of the tissue with a distal end of the suture passer. In one or more embodiments, moving an actuator of the suture passer into a second position may include manually moving the actuator of the suture passer from a first position to the second position by hand. As discussed above, in one or more embodiments, the actuator may include one or more control mechanisms, which may be used to move the actuator with the suture passer from a first position to a second position.

FIGS. 6A-6F show suturing methods in accordance with embodiments of the invention. These methods may include using suture passers to stabilize grafts on tissues.

Figure 6A:
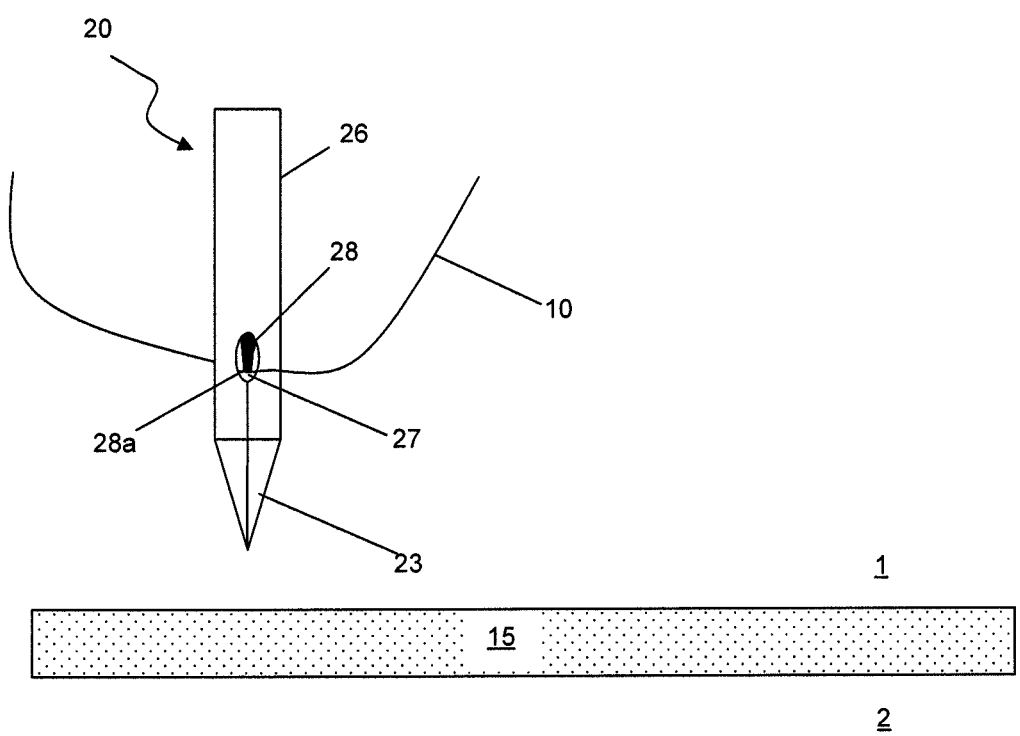
FIGS. 6A-6G show suturing methods in accordance with embodiments of the invention.

Referring to FIG. 6A, a suture passer 20 situated on side 1 of tissue 15 prior to piercing through tissue 15 at a first location is shown. As shown, the actuator 28 may be disposed within the tubular member 26 of suture passer 20. In one or more embodiments, the actuator 28 may be configured to engage or contact a first suture 10 that may be disposed through the eyelet 27. As shown, the movable jaw 23 of the suture passer 20 is in the closed position.

Figure 6B:
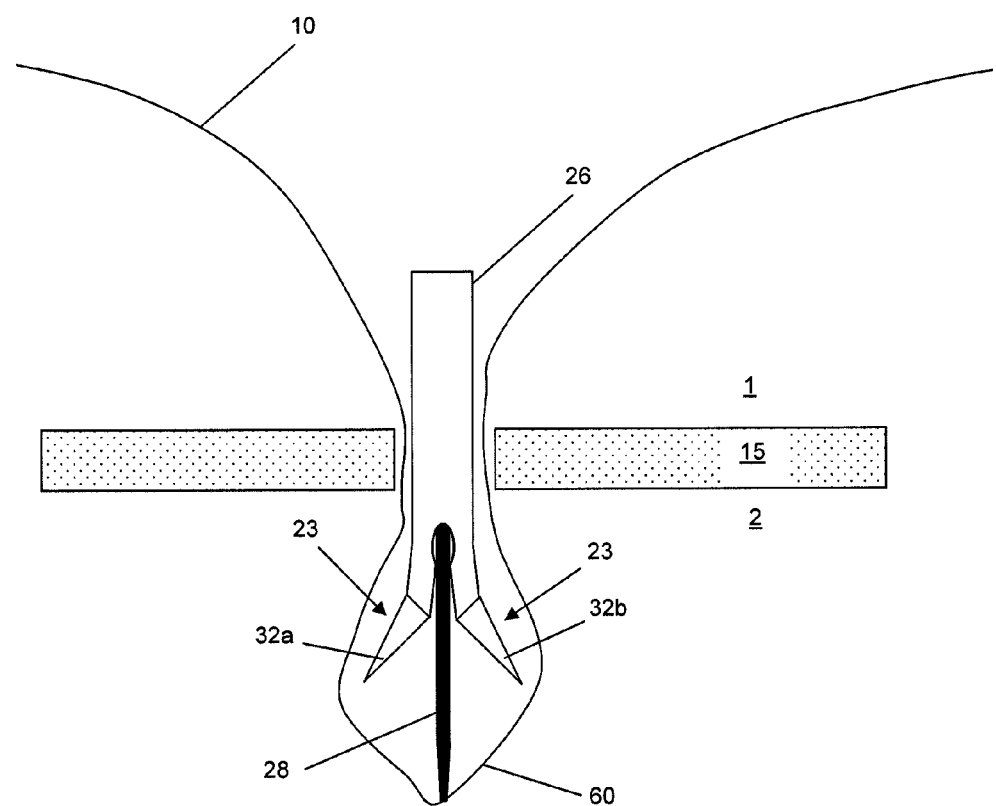

Referring to FIG. 6B, the suture passer 20 is shown after tubular member 26 has pierced through the tissue 15 at a first location, and the movable jaw 23 is in the open position. As discussed above, the actuator 28 move from the first position into the second position, as shown, and may urge the portions 32a, 32b to be in a separate relationship, which may move the movable jaw 23 into the open position. As such, the actuator 28 may advance, or move, the first suture 10 from side 1 to side 2 of the tissue 15, forming a suture loop 60. As discussed above, those having ordinary skill in the art will appreciate that a suture loop, as described herein, may not necessarily be a closed loop.

Figure 6C:
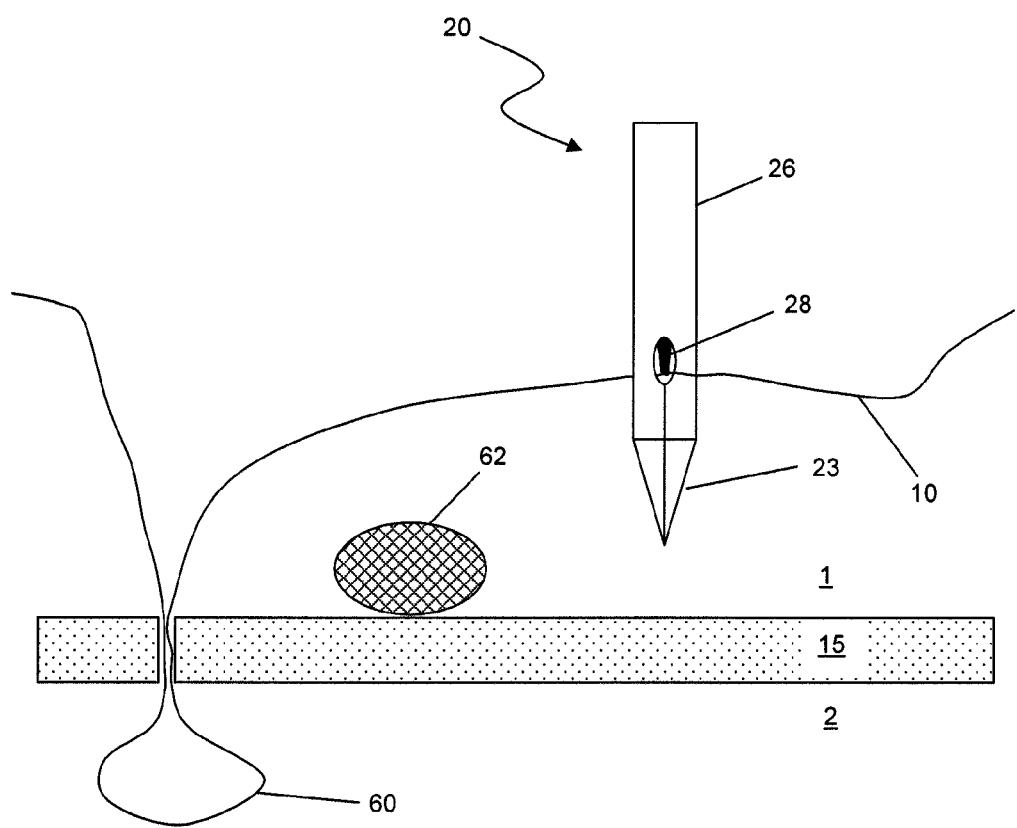

Referring to FIG. 6C, the suture passer 20 is shown after releasing the suture loop 60 on side 2 of the tissue 15. As shown, the movable jaw 23 may moved to the closed position by retracting the actuator 28 to the first position, e.g., moving the actuator in a direction that is parallel to a central axis of the tubular member 26, away from the movable jaw 23. As discussed above, in one or more embodiments, the portions 32a and 32b of the movable jaw 23 are biased to the closed position. As such, in one or more embodiments, moving the actuator 28 from the second position to the first position may cause the portions 32a, 32b to move into a proximate position, i.e., may cause the movable jaw 23 to move into the closed position. As shown, the suture passer 20 may be retracted to side 1 of tissue 15. A portion of the first suture 10 may be positioned within the eyelet of the suture passer 20, as described above. In one or more embodiments, to stabilize a first graft 62 with tissue 15, a user may repeat the method illustrated in FIG. 6A and position the suture passer 20 at a second location on side 1 of tissue 15, such that the first graft 62 may contact portion of the first suture 10 between the suture loop 60 and the suture passer 20 at the second location.

Figure 6D:
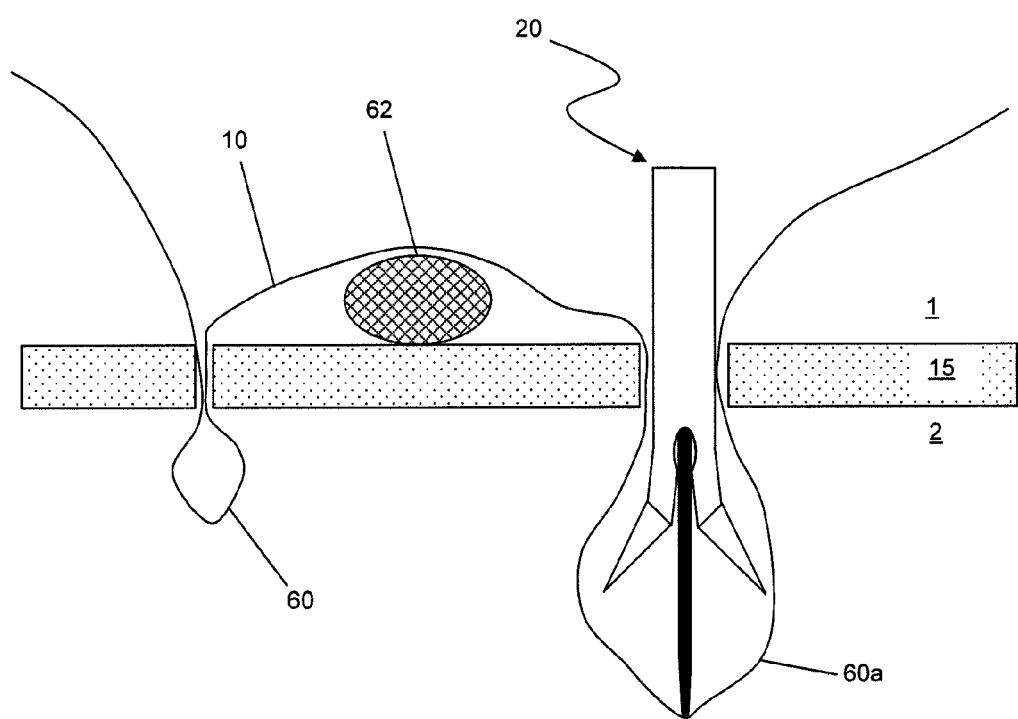

Referring to FIG. 6D, the suture passer 20 is shown after tubular member 26 has pierced through the tissue 15 at a second location, and the movable jaw 23 is in the open position. As discussed above, the suture passer 20 may pierce through tissue 15 at the second location and form a second suture loop 60a on side 2 of tissue 15 according to steps illustrated by FIG. 6B so that the first graft 62 may contact a portion of the first suture 10 between the suture loop 60 and the suture loop 60a. As discussed above, the actuator 28 move from the first position into the second position, as shown, and may urge the portions 32a, 32b to be in a separate relationship, which may move the movable jaw 23 into the open position. As such, the actuator 28 may advance, or move, the first suture 10 from side 1 to side 2 of the tissue 15, forming the suture loop 60a.

Figure 6E:
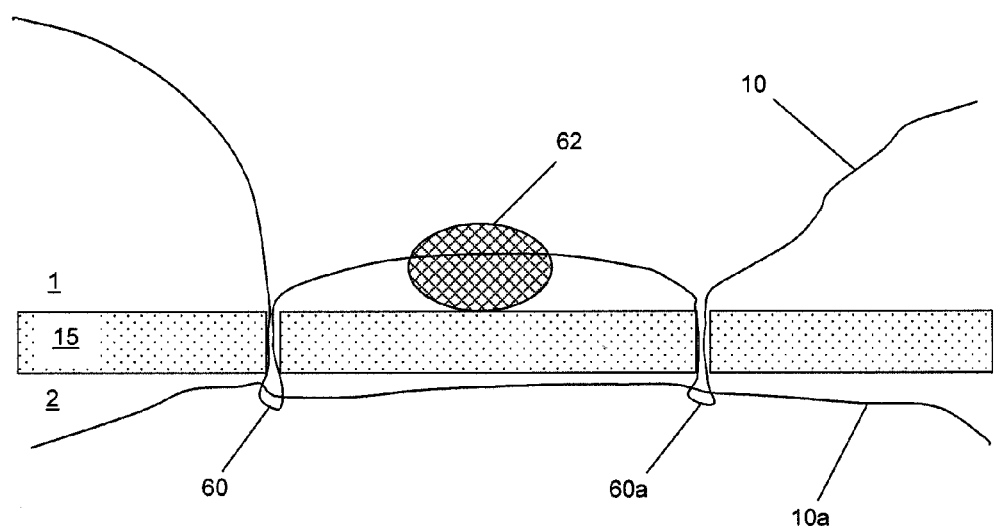

Referring to FIG. 6E, the first graft 62 secured on side 1 of tissue 15 by the first suture 10 and the second suture 10a is shown. As discussed above, the first graft 62 may be stabilized with the tissue 15 by securing or tightening both the first suture 10 on side 1 of tissue 15, and the second suture 10a on side 2 of tissue 15. As discussed above, tightening the first suture 10 and the second suture 10a may cause the first graft 62 to be bound against the tissue 15. The second suture 10a may be weaved through suture loops 60, 60a using any device known in the art. Further, as discussed above, the first suture 10 and the second suture 10a may be the same suture or different sutures.

Figure 6F:
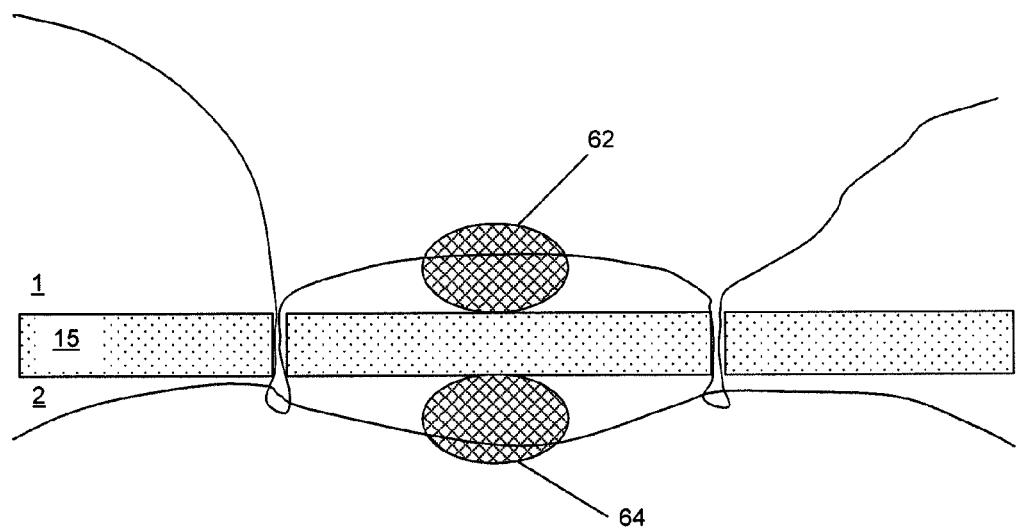

Referring to FIG. 6F a second graft 64, in addition to the first graft 62, are shown. In one or more embodiments, suture passers, in accordance with embodiments disclosed herein, may be used to stabilize the first graft 62 on side 1 of the tissue 15 and the second graft 64 on side 2 of the tissue 15 using steps illustrated by FIGS. 6A-6E and discussed above. In one or more embodiments, stabilizing the first graft 62 and the second graft may include tightening the first suture 10 and the second suture 10a, which may cause the first graft 62 and the second graft 64 to be bound against the tissue 15, on side 1 and side 2 of the tissue 15, respectively.

Figure 6G:
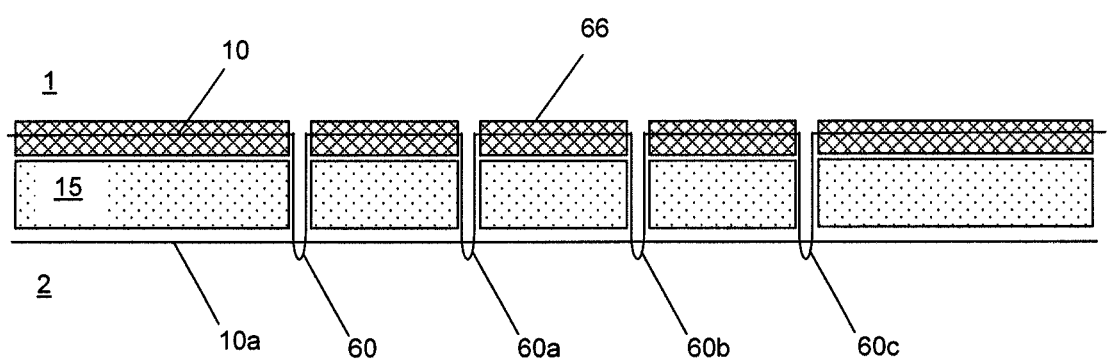

Referring to FIG. 6G, a suturing method in accordance with embodiments disclosed herein is shown. In one or more embodiments, suture passers (not shown), according to embodiments disclosed herein, may be used to stabilize a graft 66, which may be layered on side 1 of the tissue 15. A first suture 10 may be passed through both the graft 66 and the tissue 15 at multiple positions from side 1 of the tissue 15 to side 2 of the tissue 15 using the method illustrated in FIGS. 6A-6E. The first suture 10 may form multiple suture loops 60, 60a, 60b, 60c on side 2 of the tissue 15, as discussed above and shown in FIGS. 6A-6E. A second suture 10a on side 2 of tissue 15 may be weaved, threaded, moved, or passed through the suture loops 60, 60a, 60b, 60c. Those having ordinary skill in the art will appreciate that the second suture 10a may be threaded through suture loops 60, 60a, 60b, 60c, using any device or means known in the art. As discussed above, the first suture 10 and the second suture 10a may be the same suture or different sutures. The graft 66 may be stabilized by securing or tightening the first suture 10 and the second suture 10a, as discussed above. Other suturing methods in accordance with embodiments of the invention may include stabilizing multiple grafts on more than one side of tissue 15 using similar approaches, as described above.

Advantageously, embodiments disclosed herein may assist with suture passing. Suture passing may be problematic for surgeons, such as arthroscopic surgeons, because braided suture preferred by most arthroscopists may not be pushed through cannulated instruments. As a result, braided sutures usually require larger incisions and are pulled into locations because applying a push force may cause the braid to expand in diameter, thereby wedging in the instrument. Embodiments disclosed herein provide suture passers with minimum distal shaft diameter to pass sutures through tissues. With a minimum diameter of the tubular member, the suture passers may enable instruments to pass sutures through tissues with minimal damage to tissues.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A suture passer, comprising:
   a tubular member having a proximal end and a distal end and a lumen formed therein;
   an eyelet formed in the tubular member and dimensioned to receive a suture, wherein the eyelet is in communication with the lumen; and
   a slot extending between a distal end of the eyelet and the distal end of the tubular member, the slot further having opposing faces, wherein at least a portion of the opposing faces of the slot define at least two moveable jaw portions on the distal end of the tubular member;
   wherein the at least two jaw portions are adapted to move between a closed position, where the opposing faces of the slot are proximate to each other and inhibit distal motion there through of a suture positioned within the eyelet, and an open position, where the opposing faces of the slot are separated from each other and permit distal motion there through of a suture positioned within the eyelet.

2. The suture passer of claim 1, further comprising an actuator dimensioned for receipt within the lumen and moveable therein between a first position and a second position;
   wherein, in the first position, a distal end of the actuator does not engage the slot and the at least two jaw portions are in the closed position; and
   wherein, in the second position, the distal end of the actuator is interposed between the opposing faces of the slot and urges the at least two jaw portions into the open position.

3. The suture passer of claim 2, wherein a suture positioned within the eyelet is not engaged by a distal end of the actuator when the actuator is in the first position.

4. The suture passer of claim 2, wherein movement of the actuator from the first to the second position engages a suture positioned within the eyelet with a distal end of the actuator and urges the suture distally through the slot and the at least two jaw portions.

5. The suture passer of claim 2, wherein the distal end of the actuator possesses a width greater than or equal to the diameter of a suture.

6. A suture passer, comprising:
   a tubular member having a proximal end, a distal end, and a lumen extending there between;
   an eyelet extending through body of the tubular member and intersecting the lumen;
   at least two jaws formed in the distal end of the tubular member, wherein the at least two jaws are in communication with the eyelet and wherein the lumen further intersects the at least two jaws; and an actuator positioned within the lumen and moveable between a first position and a second position, the second position distal to the first position;

wherein a distal end of the actuator does not engage a proximal end of the at least two jaws in the first position; and wherein the distal end of the actuator urges the at least two jaws apart from one another in the second position.

7. The suture passer of claim 6, wherein the distal end of the actuator is positioned proximal to the eyelet in the first position.

8. The suture passer of claim 7, wherein the at least two jaws converge at the distal end of the tubular member when the actuator is in the first position.

9. The suture passer of claim 6, wherein the distal end of the adaptor engages a suture positioned within the eyelet when moved from the first position to the second position.

10. The suture passer of claim 6, wherein the diameter of the lumen decreases from the eyelet to the distal end of the at least two jaws.

11. The suture passer of claim 6, wherein the at least two jaws form a non-conical shape when the actuator is in the first position.

12. A method of suturing, comprising:

placing a suture through an eyelet of a suture passer, the suture passer comprising:

a tubular member having a proximal end, a distal end, and a lumen extending there between;

the eyelet extending through the tubular member and intersecting the lumen;

at least two jaws formed in the distal end of the tubular member, wherein the at least two jaws are in communication with the eyelet and wherein the lumen further intersects the at least two jaws; and an actuator positioned within the lumen and moveable between a first position and a second position, the second position distal to the first position;

piercing a first region of a tissue with the distal end of the suture passer while the actuator in the first position, wherein the distal end of the actuator does not engage a proximal end of the at least two jaws;

moving the actuator from the first position to the second position, wherein said movement engages the distal end of the actuator with the suture positioned within the eyelet, urges the at least two jaws apart from one another; and further urges the suture distally through the at least two jaw portions; and disposing the suture at least partially within the tissue.

13. The method of claim 12, wherein disposing the first suture at least partially within the tissue further comprises disengaging the suture from the distal end of the actuator.

14. The method of claim 12, wherein the distal end of the actuator is adapted to extend distally beyond the distal end of the tubular member when positioned in the second position.

15. The method of claim 12, wherein moving the actuator into the second position further comprises urging the at least two jaws apart by a distance greater than or equal to a diameter of the actuator.

* * * * *